United States Patent
Lewis et al.

(10) Patent No.: US 8,546,132 B1
(45) Date of Patent: Oct. 1, 2013

(54) TESTING PROBE FOR TESTING AND VALIDATION OF BIOLOGICAL KILL RATES IN REGULATED MEDICAL WASTE AUTOCLAVES

(76) Inventors: Robert W. Lewis, Charlotte, NC (US); Timothy A. Barrett, Douglassville, PA (US)

( * ) Notice: Subject to any disclaimer, the term of this patent is extended or adjusted under 35 U.S.C. 154(b) by 106 days.

(21) Appl. No.: 12/925,894

(22) Filed: Nov. 1, 2010

(51) Int. Cl.
*C12M 1/34* (2006.01)
*C12M 3/00* (2006.01)

(52) U.S. Cl.
USPC .................. 435/287.4; 422/50; 422/292

(58) Field of Classification Search
USPC ............ 422/1, 292; 435/291, 31, 287.4; 374/155; 206/178, 306; 436/1
See application file for complete search history.

(56) References Cited

U.S. PATENT DOCUMENTS

| | | | | |
|---|---|---|---|---|
| 4,591,566 A * | 5/1986 | Smith | ......................... | 435/287.4 |
| 8,043,845 B2 * | 10/2011 | Franciskovich et al. | ... | 435/287.4 |
| 2004/0247015 A1 * | 12/2004 | Wojan et al. | .................. | 374/120 |
| 2008/0043809 A1 * | 2/2008 | Herbert | ......................... | 374/163 |

* cited by examiner

*Primary Examiner* — Sean E Conley
*Assistant Examiner* — Ross Dworet
(74) *Attorney, Agent, or Firm* — John F. A. Earley, III; Frank J. Bonini, Jr.; Harding, Earley, Follmer & Frailey, P.C.

(57) ABSTRACT

An apparatus for safely and conveniently placing and retrieving biological indicators and/or computerized data tracers from deep within loads of Regulated Medical/Infectious Waste comprises a rod with a cavity for holding the biological indicators and/or computerized data tracers. Preferably, the rod is tapered to a point on one end, has a handle on the opposite end, and has a cover to enclose the cavity. Additionally, it is preferred that the rod is fitted with a movable sealing ring of soft material for sealing the area where the rod penetrates the waste load.

18 Claims, 4 Drawing Sheets

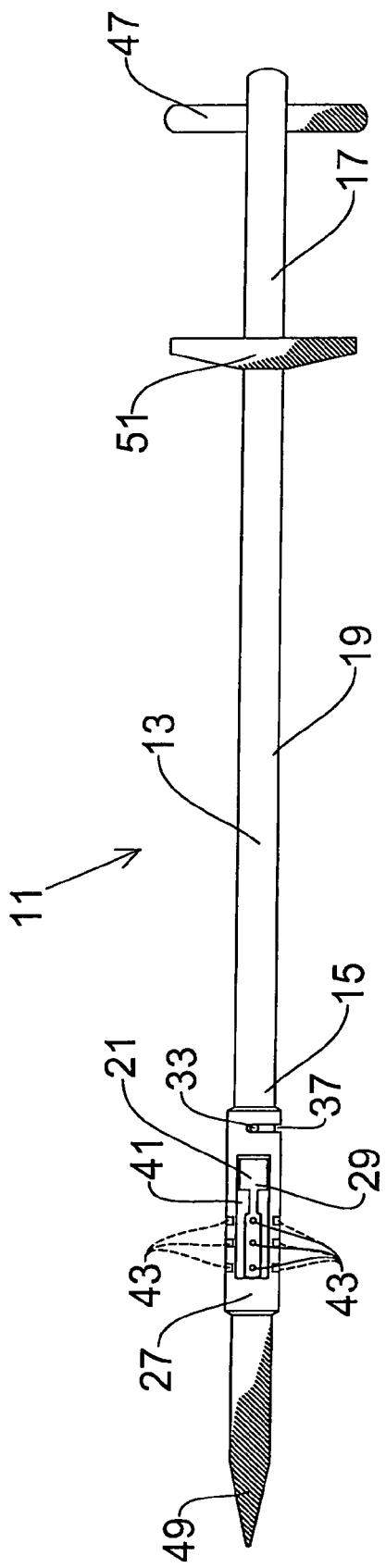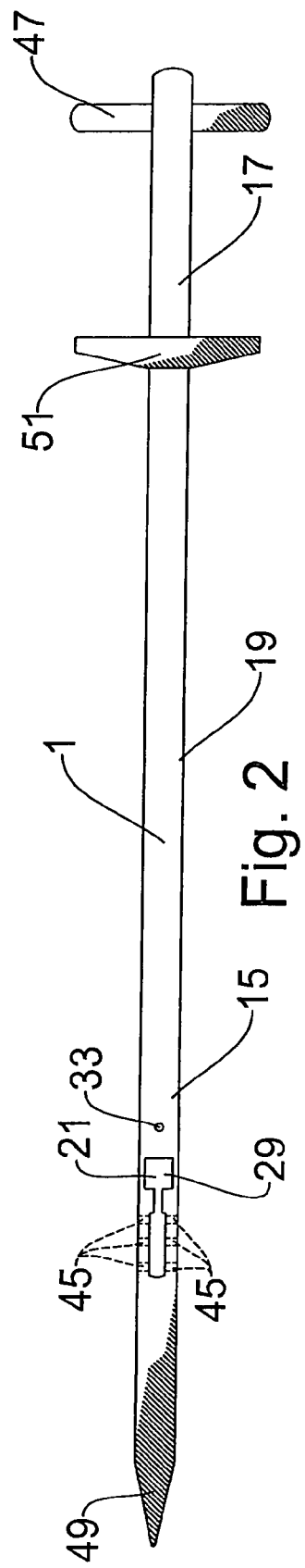

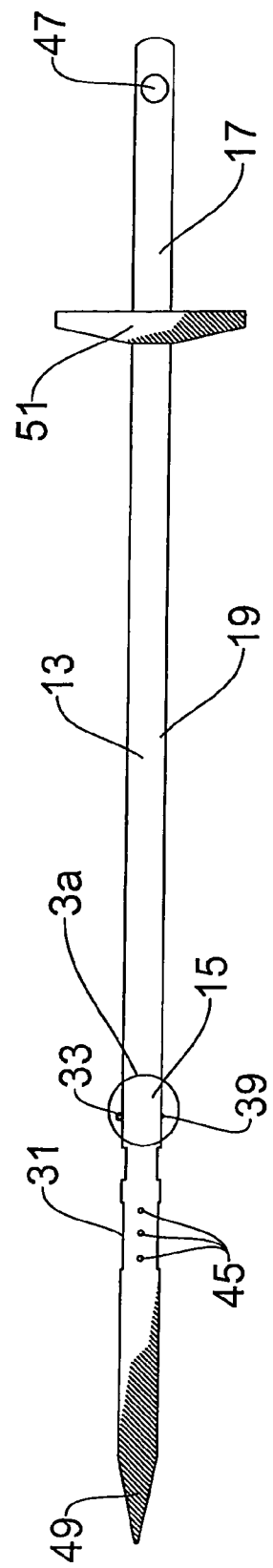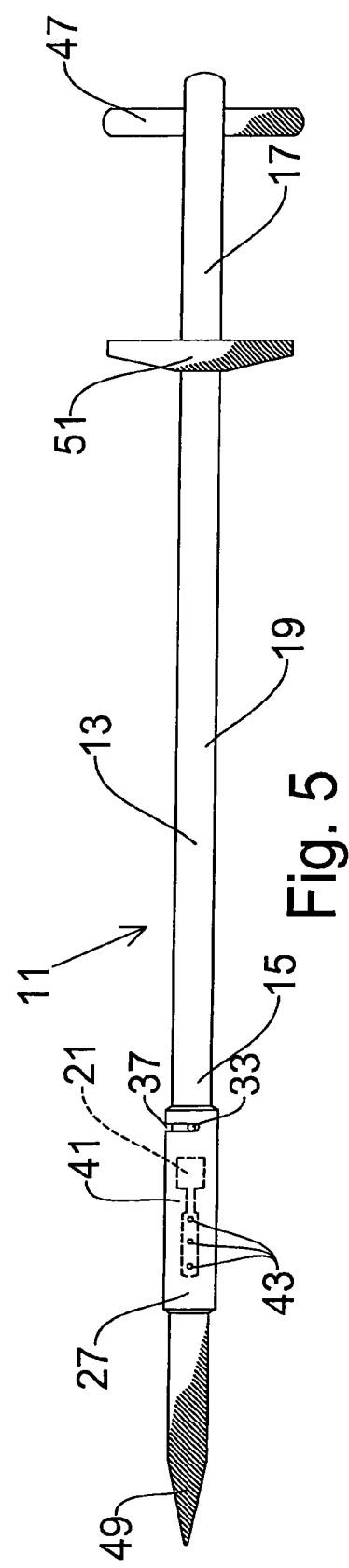

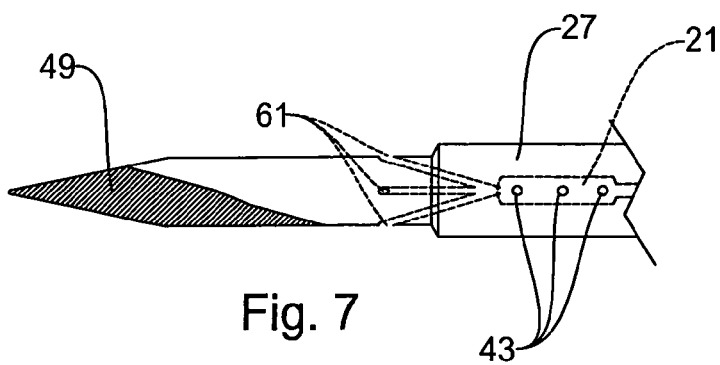
Fig. 7
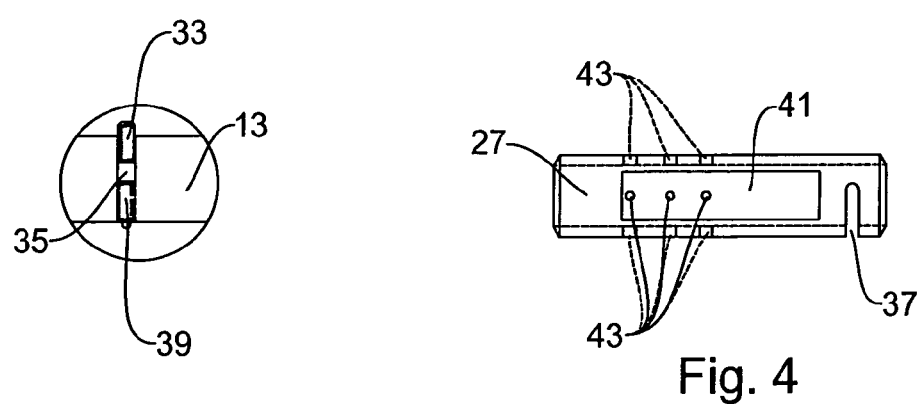
Fig. 3a
Fig. 4
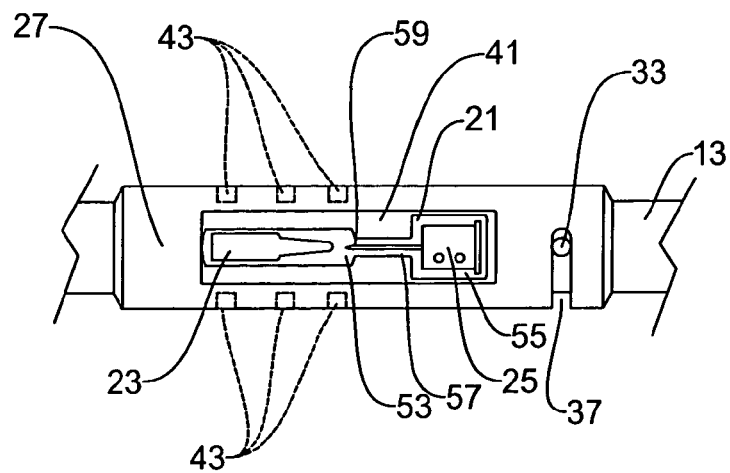
Fig. 8

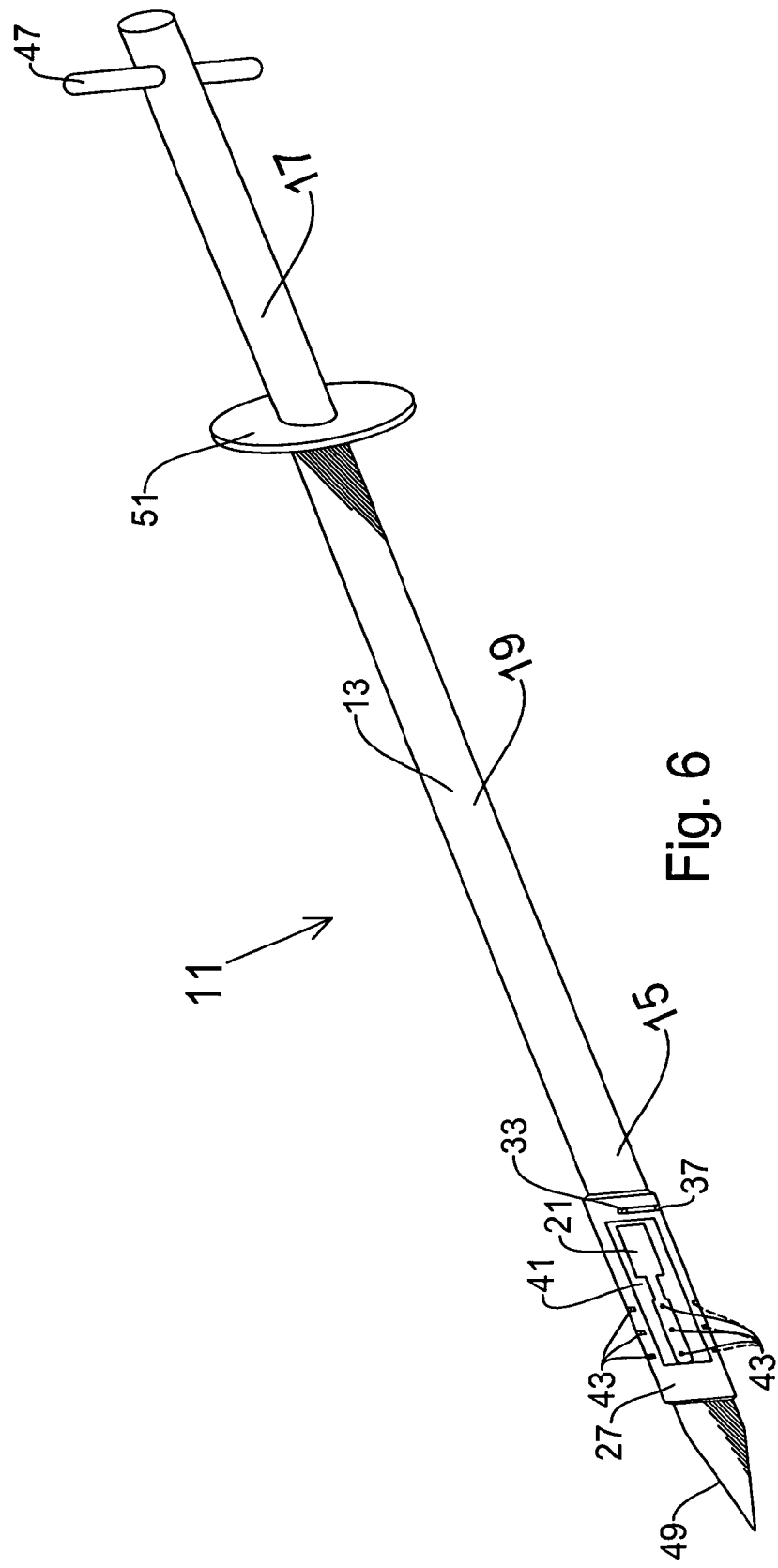

TESTING PROBE FOR TESTING AND VALIDATION OF BIOLOGICAL KILL RATES IN REGULATED MEDICAL WASTE AUTOCLAVES

BACKGROUND OF THE INVENTION

1. Field of the Invention

This invention relates to an apparatus and method for improving the safety, convenience and accuracy of the testing of autoclaves required by regulations for the treatment of Regulated Medical/Infectious Waste.

2. Description of the Prior Art

Most regulating authorities require the periodic testing of autoclaves used for the treatment of Regulated Medical/Infectious Waste. The testing is to ensure that proper treatment, residence time, temperature and spore kill are taking place. Conventionally, the testing of an autoclave used for the treatment of Regulated Medical/Infectious Waste is widely preformed by placing biological indicators on top of a cart/bin of waste, subjecting the cart/bin of waste (which has the biological indicators placed on top thereof) to a treatment (e.g., exposure to steam, or exposure to steam and vacuum such as in U.S. Pat. Nos. 7,815,851 and 6,867,393, both of which are incorporated herein by reference) in the autoclave, and then analyzing the biological indicators to determine if the waste has been properly treated. Because this practice readily exposes the biological indicators positioned on top of the waste to steam during the autoclave treatment, the biological indicators typically reflect that the autoclave treatment of the waste was successful (e.g., a "No Growth" test result). However, while this conventional testing method is safe and convenient, it is often lacking in accuracy in that it may provide a test result that is not reflective of the effectiveness of the treatment within (as opposed to on top of) the waste.

SUMMARY OF THE INVENTION

It is an object of this invention to provide a safe and convenient means for placing deep within a load of Regulated Medical/Infectious Waste and subsequently retrieving therefrom biological indicators and computerized data tracers.

Another object of this invention is to provide a means to facilitate accurately testing the efficacy of autoclaves used for the treatment or Regulated Medical/Infectious Waste.

These and other objects are provided by our invention which is set out below.

In a preferred embodiment of our invention, our inventive autoclave test probe comprises a rod with a handle on one end to facilitate handling of the probe especially during use of the probe (e.g., insertion of the probe into a load of waste and removal of the probe from a load of waste), a tapered point on the opposite end to permit the probe to easily puncture through boxes and bags within the waste load, a cavity formed in the rod for holding one or more biological indicators and/or a computerized data tracer, an opening or bore formed in the rod forming an entrance to the cavity, a cover movably mounted on the rod for opening and closing the entrance to the cavity, and a movable sealing ring of softer material for sealing the area where the probe enters the waste load.

In this preferred embodiment, the cover for the cavity is tubular in shape and is movably mounted on the rod. In this preferred embodiment, at least one pin or the like (e.g., dowel, set screw) is positioned on the rod for engaging at least one slot or detent formed in the cover for maintaining the cover on the rod. Preferably, the cover is rotationally or longitudinally held in the closed position, covering the cavity, with a spring-loaded detent pin which engages a detent on the inside of the tubular cover. The cover has an opening formed therein which is of sufficient size to allow a biological indicator and/or computerized data tracer to be inserted through the opening into the cavity when the cover is in an open position (that is, when the cover is positioned on the rod such that the opening in the cover is aligned with the entrance to the cavity). Preferably, holes are formed in the cover, and bores are formed in the rod extending between the cavity and the exterior of the rod, the holes in the cover being aligned with the bores in the rod when the cover is in a closed position (that is, when the cover is positioned on the rod to close the entrance to the cavity) to create passageways between the cavity and the exterior of the probe to allow air, vapors, or steam to pass into and through the cavity.

Further, the cavity preferably is sized to accept the type of biological indicator selected by the user. The cavity also may be sized to permit the inclusion of a mechanical or electronic measuring or recording device (e.g., a computerized data tracer) that measures and/or measures and records the autoclave treatment conditions applied within the waste load during the autoclave treatment.

Preferably, additional bores that preferably are smaller than the bores formed in the rod that allow air, vapors, steam to enter and pass through the cavity are formed in the rod and extend from the cavity to the exterior of the probe, preferably between the end of the cavity that is closer to the end of the probe having the tapered point and the exterior of the probe between where the cavity is located and the end of the probe having the tapered point, to allow condensate which might accumulate in the cavity to drain from the cavity.

BRIEF DESCRIPTION OF THE DRAWINGS

FIG. 1 is a view in side elevation of a preferred autoclave test probe constructed in accordance with the invention.

FIG. 2 is the side elevational view of the preferred autoclave test probe shown in FIG. 1, except without the cavity cover for the probe being installed on the probe.

FIG. 3 is a view in side elevation of the preferred autoclave test probe (except without the cavity cover for the probe being installed on the probe) shown in FIG. 2, after the probe has been rotated 90 degrees so that the portion of the dowel or setscrew 6 that extends from the rod 1 now points to the top of the drawing sheet.

FIG. 3*a* is an enlarged partial view taken in cross-section of the portion of the autoclave test probe contained in the circle 3*a* shown in FIG. 3.

FIG. 4 is a view is side elevation of the cavity cover shown in FIG. 1.

FIG. 5 is a view in side elevation of the preferred autoclave test probe shown in FIG. 1, after the cover 27 has been rotated to a closed position to close the entrance 31 to the cavity or chamber 21 (which is shown in the fathom).

FIG. 6 is a perspective view of the autoclave test probe shown in FIG. 1.

FIG. 7 is an enlarged view of the first end portion of the autoclave test probe highlighting optional condensate drainage bores formed in the rod extending between the cavity and the exterior of the probe to permit condensate that might accumulate in the cavity to drain from the cavity.

FIG. 8 is an enlarged view of the first end portion of the autoclave test probe with its cover 27 in an open position showing positioned in the cavity or chamber 21 of the probe a biological indicator 23 and a device 25 for measuring and/or measuring and recording autoclave treatment conditions during an autoclave treatment.

DETAILED DESCRIPTION

Turning to the drawings, there is shown our inventive apparatus or autoclave test probe 11 for testing autoclaves used for the treatment of Regulated Medical/Infectious Waste. In this preferred embodiment of the invention shown in the drawings, the apparatus 11 has a rod 13 having a first end portion 13, a second end portion 15, and a middle portion 17 located between the first and second end portions 13 and 15.

The rod 13 has a cavity or chamber 21 formed therein, preferably in the first end portion of the rod 13, for holding one or more biological indicators 23 (e.g., ampoules, spore strips, etc.) and/or a device 25 (e.g., a computerized data tracer) that measures and/or measures and records the autoclave treatment conditions (e.g., temperature, pressure, and/or humidity) applied within the waste load during treatment in an autoclave.

The apparatus 11 also has means for maintaining the one or more biological indicators 23 and/or the device 25 in the cavity or chamber 21 when desired. Examples of such means include doors mounted on the rod 13 for closing off the cavity or chamber 21 when desired, a cage for holding the one or more biological indicators 23 and/or the device 25 wherein the cage may be removably press-fit into the cavity 21, or a cover (such as a cover 27 which is described below).

In the preferred embodiment of the invention shown in the drawings, the cavity or chamber 21 is formed by a slot 29 that extends completely through the rod 13, which creates at one end of the slot 29 an entrance 31 to the cavity or chamber 21, the entrance 31 being of sufficient size to permit at least one biological indicator 23 and/or device 25 to be inserted through the entrance 31 to be placed inside the cavity or chamber 21. In the preferred embodiment shown in the drawings, the means for maintaining the one or more biological indicators 23 and/or the device 25 in the cavity or chamber 21 when desired is a cover 27. The cover 27, which is movably mounted on the rod 13, forms the back wall of the cavity or chamber 21 and allows for the entrance 31 to the cavity or chamber 21 to be opened and closed, as desired. Alternatively, the cavity or chamber 21 may be formed by a slot that extends only partially into the rod 13 such that the back wall of the cavity or chamber 21 is formed by the portion of the rod 13 at the end of the slot.

Regarding cover 27, the apparatus 11 is provided with means for maintaining the cover 27 on the rod 13. One preferred example of such means is where pins are provided on the rod 13 and slots are provided on the cover 27, as shown in the drawings, to maintain the cover 27 on the rod 13 and facilitate rotation of the cover 27 back and forth between an open position and a closed position on the rod 13. Specifically, in the preferred embodiment of the invention shown in the drawings, the cover 27 is rotatably mounted on the rod 13 preferably using a pin 33 or the like (e.g., a pin or dowel or set screw) press-fit into one end of a bore 35 extending through the rod 13 that engages a slot 37 formed in the cover 27, and a spring-loaded detent pin 39 or the like positioned in and extending from the other end of the bore 35 that engages a groove formed on the inside surface of the cover 27, the groove having a detent formed at one end of the groove to receive the ball of the detent pin 39 when the cover 27 is positioned in a closed position over the entrance 31 of the cavity or chamber 21. Another example of such means for maintaining the cover 27 on the rod 13 is where a pair of snap rings or similar retainer mechanism is mounted on the rod 13 with one of the pair positioned at one end of the cover 27 and the other of the pair positioned at the other end of the cover 27 to engage and hold the cover 27 on the rod 13.

In the preferred embodiment shown in the drawings, the cover 27 is provided with an opening 41 formed therein which is of sufficient size to allow at least one biological indicator 23 and/or a device 25 to be inserted through it to permit the at least one biological indicator 23 and/or a device 25 to be inserted into the cavity or chamber 21 through its entrance 31 when the cover 27 has been rotated into an open position placing the opening 41 of the cover 27 into alignment with the entrance 31 of the cavity or chamber 21.

After at least one biological indicator 23 and/or a device 25 have been placed in the cavity or chamber 21, the cover 27 may be rotated into a closed position where the opening 41 of the cover 27 is no longer in alignment with the entrance 31 of the cavity or chamber 21 to secure or maintain the at least one biological indicator 23 and/or the device 25 in the cavity or chamber 21.

Preferably, holes 43 are formed in the cover 27, and bores 45 are formed in the rod 13 extending between the cavity 21 and the exterior of the rod 13, and the placement of the holes 43 and the bores 45 is such that the holes 43 in the cover 27 are aligned with the bores 45 in the rod 13 when the cover 27 is in a closed position (that is, when the cover 27 is positioned on the rod 13 to close the entrance 31 to the cavity 21) to create passageways between the cavity 21 and the exterior of the apparatus 11 to allow air, vapors, or steam to pass into and through the cavity 21.

Preferably, the autoclave test probe 11 has a handle 47 formed in or mounted on the second end portion 17 of the rod 13 to facilitate handling of the probe 11 especially during use of the probe 11 (e.g., insertion of the probe 11 into a load of waste and removal of the probe 11 from a load of waste). Further, preferably, the probe 11 has a tapered point 49 formed on the end of the first end portion 15 of the rod 13 to permit the probe 11 to easily puncture through boxes and bags within the waste load.

Preferably, the apparatus 11 is provided with a sealing ring 51 slidably mounted on the rod 13 for sealing the load of waste where the rod 13 penetrates the load of waste when the apparatus 11 is in use.

The cavity or chamber 21 preferably is positioned in the first end portion 15 of the rod 13 near the tapered point 49. Preferably, the cavity is sized to hold the type of biological indicator 23 and/or the type of device 25 selected by the user of the apparatus 11. In the preferred embodiment of the invention shown in the drawings, the cavity 21 has a first portion 53 for holding at least one biological indicator 23, a second portion 55 for holding a device 25 for measuring and/or measuring and recording autoclave treatment conditions during the autoclave treatment, and a third portion 57 connecting the first portion 53 of the cavity 21 to the second portion 55 of the cavity 21 that permits a sensor 59 from the device 25 for measuring and/or measuring and recording autoclave treatment conditions during an autoclave treatment when such device 25 is held in the second portion 55 of the cavity 21 to extend into the first chamber 53 but otherwise substantially blocks such a device 25 from entering the first portion 53 of the chamber 21 from the second portion 55 of the cavity 21 via the third portion 57 of the cavity, thereby avoiding damage to a biological indicator 23 by being hit by a main portion of the device 25 when the apparatus 11 is in use.

As only shown in FIG. 7 for purposes of clarity, preferably, additional bores or condensate drainage holes 61 that preferably are smaller than the bores 45 formed in the rod 13 that allow air, vapors, steam to enter and pass through the cavity 21 are formed in the rod 13 and extend from the cavity 21 to the exterior of the probe or apparatus 11, preferably between the end of the cavity 21 that is closer to the end of the probe or apparatus 11 having the tapered point 49 and the exterior of the probe or apparatus 11 between where the cavity 21 is located and the end of the probe or apparatus 11 having the tapered point 49, to allow condensate which might accumulate in the cavity 21 to drain from the cavity 21.

Preferably, the rod 13, cover 27, and handle 47 are made from a polymeric material, such as amorphous thermoplastic polyetherimide (PEI), such as that sold under the mark Ultem 1000, and the sealing ring 51 is made from a soft material such as a silicone rubber.

In use, the apparatus 11 may be used in the testing of autoclaves used for the treatment of Regulated Medical/Infectious Waste in accordance with our inventive method of placing deep within the load of Regulated Medical/Infectious Waste and subsequently retrieving therefrom at least one biological indicator 23 and/or a device 25 for measuring and/or measuring and recording autoclave treatment conditions during an autoclave treatment to determine efficacy of the autoclave treatment. In accordance with the method, at least one biological indicator 23 and/or a device 25 for measuring and/or measuring and recording conditions during an autoclave treatment is placed into the cavity 21 of the apparatus 11, and then the at least one biological indicator 23 and/or the device 25 for measuring and/or measuring and recording conditions during an autoclave treatment is secured or maintained (e.g., by closing (e.g., rotating the cover 27 to a closed position) the cover 27) in the cavity 21 of the apparatus 11. Then, the apparatus 11 is inserted into the load of waste so that the cavity or chamber 21 holding the at least one biological indicator 23 and/or the device 25 is positioned deep within the load of waste, and, when the apparatus 11 is provided with a sealing ring 51, so that the sealing ring 51 seals the load of waste where the rod 13 penetrates the load of waste. After the portion of the apparatus 11 having the cavity or chamber 21 containing at least one biological indicator 23 and/or a device 25 has been inserted deeply into the load of waste, the load of waste (with the apparatus 11 being inserted therein) is subjected to an autoclave treatment. After the autoclave treatment, the apparatus 11 is removed from the load of waste, and the at least one biological indicator 23 and/or the device 25 for measuring and/or measuring and recording autoclave treatment conditions during an autoclave treatment is removed from the cavity 21 of the apparatus 11 for use in determining efficacy of the autoclave treatment by, for example, testing (e.g., by incubating) the biological indicator(s) 23 that have been removed from the cavity 21 after being subjected to the autoclave treatment with the load of waste to determine whether a test organism has been destroyed, and/or analyzing the autoclave treatment conditions measured by the device 25.

The invention claimed is:

1. An apparatus for testing of autoclaves used for treating Regulated Medical/Infectious Waste, comprising a rod having a first end portion, a second end portion, and a middle portion located between the first end portion and the second end portion, a cavity formed in the rod holding a biological indicator and a device that measures and/or measures and records autoclave treatment conditions applied within a load of waste during treatment in an autoclave, the cavity having an entrance thereto through which a biological indicator and a device that measures and/or measures and records autoclave treatment conditions applied within a load of waste during treatment in an autoclave inserted into the cavity prior to use of the apparatus and removed from the cavity after use of the apparatus, the cavity having a first portion holding at least one biological indicator, a second portion holding a device for measuring and/or measuring and recording autoclave treatment conditions during an autoclave treatment, and a third portion connecting the first portion of the cavity to the second portion of the cavity that permits a sensor from the device for measuring and/or measuring and recording autoclave treatment conditions during an autoclave treatment when such device is held in the second portion of the cavity to extend into the first portion of the cavity but otherwise substantially blocks such a device from entering the first portion of the cavity from the second portion of the cavity via the third portion of the cavity, thereby avoiding damage to a biological indicator by being hit by a main portion of the device when the apparatus is in use, and means for maintaining the biological indicator and the device that measures and/or measures and records autoclave treatment conditions applied within a load of waste within the cavity.

2. The apparatus of claim 1,
said means being a cover movably mounted on the rod for opening and closing the entrance to the cavity.

3. The apparatus of claim 1, further including
a handle located on the second end portion of the rod.

4. The apparatus of claim 1,
the first end portion having an end that is tapered to a point.

5. The apparatus of claim 4,
the cavity in the rod being positioned in the first end portion of the rod near the end of the first end portion of the rod that is tapered to a point.

6. The apparatus of claim 2,
the cover having an opening extending through it that is sized to permit access to the cavity when the cover is moved into an open position over the entrance to the cavity.

7. The apparatus of claim 2, further including
holes formed in the cover and bores in the rod, the holes in the cover being aligned with the bores in the rod when the cover is in a closed position to create passageways between the cavity and the exterior of the apparatus to permit flow of air, vapor, liquid or steam into and through the cavity.

8. The apparatus of claim 6,
the cover being rotatably mounted on the rod, wherein the cover may be rotated into an open position on the rod to align the opening in the cover with the entrance to the cavity to gain access to the cavity via the entrance thereto, and wherein the cover may be rotated into a closed position on the rod to take the opening in the cover out of alignment with the entrance to the cavity to close the entrance to the cavity with the cover.

9. The apparatus of claim 8, further including
at least one pin positioned on the rod for engaging a slot formed in the cover for maintaining the cover on the rod.

10. The apparatus of claim 1, further including
a sealing ring slidably mounted on the rod for sealing where the rod penetrates a load of waste when the rod is in use.

11. The apparatus of claim 1, further including
a biological indicator positioned in the cavity formed in the rod.

12. The apparatus of claim 11, further including
a device for measuring and/or measuring and recording autoclave treatment conditions applied within a load of waste during an autoclave treatment.

13. The apparatus of claim 1, further including
a device for measuring and/or measuring and recording autoclave treatment conditions during an autoclave treatment.

14. A method of placing within a load of Regulated Medical/Infectious waste and subsequently retrieving therefrom a biological indicator and/or a device for measuring and/or measuring and recording autoclave treatment conditions during an autoclave treatment to determine efficacy of an autoclave treatment, comprising the steps of
providing the apparatus of claim 1, maintaining the at least one biological indicator and the device for measuring and/or measuring and recording autoclave treatment conditions during an autoclave treatment in the cavity of the apparatus,
inserting the apparatus into the load of waste so that the cavity containing the at least one biological indicator and the device for measuring and/or measuring and recording autoclave treatment conditions during an autoclave treatment is located within the load of waste,
subjecting the load of waste, with the apparatus being inserted therein, to an autoclave treatment, removing the apparatus from the load of waste, and removing the at least one biological indicator and the device for measuring and/or measuring and recording autoclave treatment conditions during an autoclave treatment from the cavity of the apparatus for use in determining efficacy of the autoclave treatment.

15. An apparatus for testing of autoclaves used for treating Regulated Medical/Infectious Waste, comprising
a rod having a first end portion, a second end portion, and a middle portion located between the first end portion and the second end portion,
a cavity formed in the rod holding a biological indicator and a device that measures and/or measures and records autoclave treatment conditions applied within a load of waste during treatment in an autoclave,
the cavity having an entrance thereto through which a biological indicator and a device that measures and/or measures and records autoclave treatment conditions applied within a load of waste during treatment in an autoclave inserted into the cavity prior to use of the apparatus and removed from the cavity after use of the apparatus,
the cavity having a first portion holding at least one biological indicator, a second portion holding a device for measuring and/or measuring and recording autoclave treatment conditions during an autoclave treatment, and a third portion connecting the first portion of the cavity to the second portion of the cavity that permits a sensor from the device for measuring and/or measuring and recording autoclave treatment conditions during an autoclave treatment when such device is held in the second portion of the cavity to extend into the first portion of the cavity but otherwise substantially blocks such a device from entering the first portion of the cavity from the second portion of the cavity via the third portion of the cavity, thereby avoiding damage to a biological indicator by being hit by a main portion of the device when the apparatus is in use,
means for maintaining the biological indicator and the device that measures and/or measures and records autoclave treatment conditions applied within a load of waste within the cavity, and
sealing ring means slidably mounted on the rod for sealing where the rod penetrates a load of waste when the rod is in use.

16. An apparatus for testing of autoclaves used for the treatment of Regulated Medical/Infectious Waste comprising, a rod having a first end portion, a second end portion, and a middle portion located between the first end portion and the second end portion,
a handle located on the second end portion of the rod,
the first end portion of the rod having an end that is tapered to a point, the point being at the end of the first end portion of the rod,
a cavity formed in the rod holding a biological indicator and a device that measures and/or measures and records autoclave treatment conditions applied within a load of waste during treatment in an autoclave,
the cavity having an entrance thereto through which a biological indicator and a device that measures and/or measures and records autoclave treatment conditions applied within a load of waste during treatment in an autoclave may be inserted into the cavity prior to use of the apparatus and removed from the cavity after use of the apparatus,
the cavity having a first portion holding at least one biological indicator, a second portion holding a device for measuring and/or measuring and recording autoclave treatment conditions during an autoclave treatment, and a third portion connecting the first portion of the cavity to the second portion of the cavity that permits a sensor from the device for measuring and/or measuring and recording autoclave treatment conditions during an autoclave treatment when such device is held in the second portion of the cavity to extend into the first portion of the cavity but otherwise substantially blocks such a device from entering the first portion of the cavity from the second portion of the cavity via the third portion of the cavity, thereby avoiding damage to a biological indicator by being hit by a main portion of the device when the apparatus is in use,
a cover movably mounted on the rod for opening and closing the entrance to the cavity,
the cover having an opening formed therein sized to permit access to the cavity when the cover is moved into an open position over the entrance of the cavity,
the cover having holes formed therein and the rod having bores formed therein, the holes in the cover being aligned with the bores in the rod when the cover is in a closed position to create passageways between the cavity and the exterior of the apparatus to permit the flow of air, vapor, liquid, or steam into and through the cavity,
at least one pin positioned on the rod for engaging at least one slot formed in the cover for maintaining the cover on the rod, and
a sealing ring slidably mounted on the rod for sealing where the rod penetrates a load of waste when the rod is in use.

17. The apparatus of claim 8, further including a pin positioned on the rod for engaging a slot formed in the cover for maintaining the cover on the rod, the slot having a first end portion and a second end portion, the pin engaging the first end portion of the slot when the cover is rotated around the rod into an open position on the rod to align the opening in the cover with the entrance to the cavity to gain access to the cavity via the entrance thereto, and the pin engaging the second end portion of the slot when the cover is rotated around the rod into a closed position on the rod to take the opening in the cover out of alignment with the entrance to the cavity to close the entrance to the cavity with the cover.

18. The apparatus of claim 15, said maintaining means being a cover movably mounted on the rod for opening and closing the entrance to the cavity, the cover having an opening extending through it that is sized to permit access to the cavity when the cover is moved into an open position over the entrance to the cavity, the cover being rotatably mounted on the rod, wherein the cover may be rotated into an open position on the rod to align the opening in the cover with the entrance to the cavity to gain access to the cavity via the entrance thereto, and wherein the cover may be rotated into a closed position on the rod to take the opening in the cover out of alignment with the entrance to the cavity to close the entrance to the cavity with the cover, and further including a pin positioned on the rod for engaging a slot formed in the cover for maintaining the cover on the rod, the slot having a first end portion and a second end portion, the pin engaging the first end portion of the slot when the cover is rotated around the rod into an open position on the rod to align the opening in the cover with the entrance to the cavity to gain access to the cavity via the entrance thereto, and the pin engaging the second end portion of the slot when the cover is rotated around the rod into a closed position on the rod to take the opening in the cover out of alignment with the entrance to the cavity to close the entrance to the cavity with the cover.

\* \* \* \* \*